(12) United States Patent
Platica et al.

(10) Patent No.: US 7,510,707 B2
(45) Date of Patent: Mar. 31, 2009

(54) PAR, A NOVEL MARKER GENE FOR BREAST AND PROSTATE CANCERS

(75) Inventors: Micsunica Platica, New York, NY (US); Ovidu Platica, New York, NY (US); James F. Holland, Scarsdale, NY (US)

(73) Assignee: New York University Mt. Sinai School of Medicine, New York, NY (US)

( * ) Notice: Subject to any disclaimer, the term of this patent is extended or adjusted under 35 U.S.C. 154(b) by 76 days.

(21) Appl. No.: 10/178,389

(22) Filed: Jun. 24, 2002

(65) Prior Publication Data

US 2003/0005471 A1 Jan. 2, 2003

Related U.S. Application Data

(63) Continuation of application No. 09/467,262, filed on Dec. 20, 1999, now abandoned.

(51) Int. Cl.
*A61K 39/395* (2006.01)

(52) U.S. Cl. .............. 424/130.1; 424/135.1; 424/139.1; 424/141.1

(58) Field of Classification Search ................. 530/350, 530/387.1; 424/130.1; 514/2
See application file for complete search history.

(56) References Cited

FOREIGN PATENT DOCUMENTS

JP 10-210983 8/1998

OTHER PUBLICATIONS

Alberts et al. Molecular Biology of the Cell, 3rd edition, 1994, p. 465.*
Shantz and Pegg Int J of Biochem and Cell Biol., 1999, vol. 31, pp. 107-122.*
McClean and Hill Eur J of Cancer, 1993, vol. 29A, pp. 2243-2247.*
Fu et al EMBO Journal, 1996, vol. 15, pp. 4392-4401.*
Definition of "inhibit" in Merriam-Webster Online downloaded on Sep. 23, 2005 from the world wide web m-w.com.*
Mehren et al., (Annu. Rev. Med., 2003, vol. 54, pp. 343-369).*
Alberts, "Molecular Biology of the Cell, 3rd edition," p. 465, 1994.
Blok et al., "Isolation of cDNAs that are differentially expressed between androgen-dependent and androgen-independent prostate carcinoma cells using differential display PCR," Prostate 26:213-224, 1995.
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111:2129-2138, 1990.
Bussemarkers et al., "Differential expression of vimentin in rat prostatic tumors," Biochem. Biophys. Res. Commun. 182:1254-1259, 1992.
Campbell, "Monoclonal Antibody Technology," Elsevier Science Publishers, pp. 1-32, 1984.
Chang et al., "Differentially expressed genes in androgen-dependent and -independent prostate carcinomas," Cancer Res., 57:4075-4081, 1997.
Chuaqui et al., "Identification of a novel transcript up-regulated in a clinically aggressive prostate carcinoma," Urology, 50:302-307, 1997.
Colman, "Effects of amino acid sequence changes on antibody-antigen interactions," Res. Immunol. 145:33-36, 1994.
Crawford et al., "Endocrine therapy of prostate cancer: optimal form and appropriate timing," J. Clin. Endocrinol. Metab. 80:1062-1078, 1995.
Fu et al., "Translational regulation of human p53 gene expression," EMBO J. 15:4392-4401, 1996.
Geck et al., "Expression of novel genes linked to the androgen-induced, proliferative shutoff in prostate cancer cells," J. Steroid Biochem. Mol. Biol., 63:211-218, 1997.
GenBank Accession No. AF115850, PAR submitted by Platica et al., Dec. 21, 1998; updated May 17, 2000.
GenBank Accession No. AI333776, EST sequences of NCI clone submitted by Robert Strausberg, Dec. 28, 1998; updated Feb. 13, 1999.
GenBank Accession No. AI354691, EST sequences of NCI clone submitted by Robert Strausberg, Jan. 4, 1999; updated Feb. 13, 1999.
GenBank Accession No. R01857, EST sequence submitted by R. K. Wilson, WashU-Merck EST Project, Mar. 31, 1995.
Gittes, "Carcnimoa of the prostate," New Engl. J. Med. 324:236-245, 1991.
Harlow et al., "Antibodies, A Laboratory Manual," pp. 72-79, 98, 100-101, 105, 115-117, and 592, 1998.
Hatakeyama et al., EMBL AB016492, "hjTB, a novel membrane protein at 1q21 rearranged in a jumping translocation," Oct. 9, 1998.

(Continued)

*Primary Examiner*—Misook Yu
(74) *Attorney, Agent, or Firm*—Marshall, Gerstein & Borun LLP

(57) ABSTRACT

The present invention relates to a gene selectively expressed in malignant cells and associated with the development of androgen resistance in prostate cancer. Levels of the gene, termed "PAR" (for Prostate Androgen Regulated), its RNA transcript, and its protein product are all present at increased levels in malignant cells, such as breast cancer and prostate cancer cells. The present invention provides for PAR nucleic acid molecules and proteins, for antibodies that specifically bind to PAR proteins, and to methods for diagnosing and treating cancers that utilize such molecules.

25 Claims, 8 Drawing Sheets

OTHER PUBLICATIONS

Figure 1:
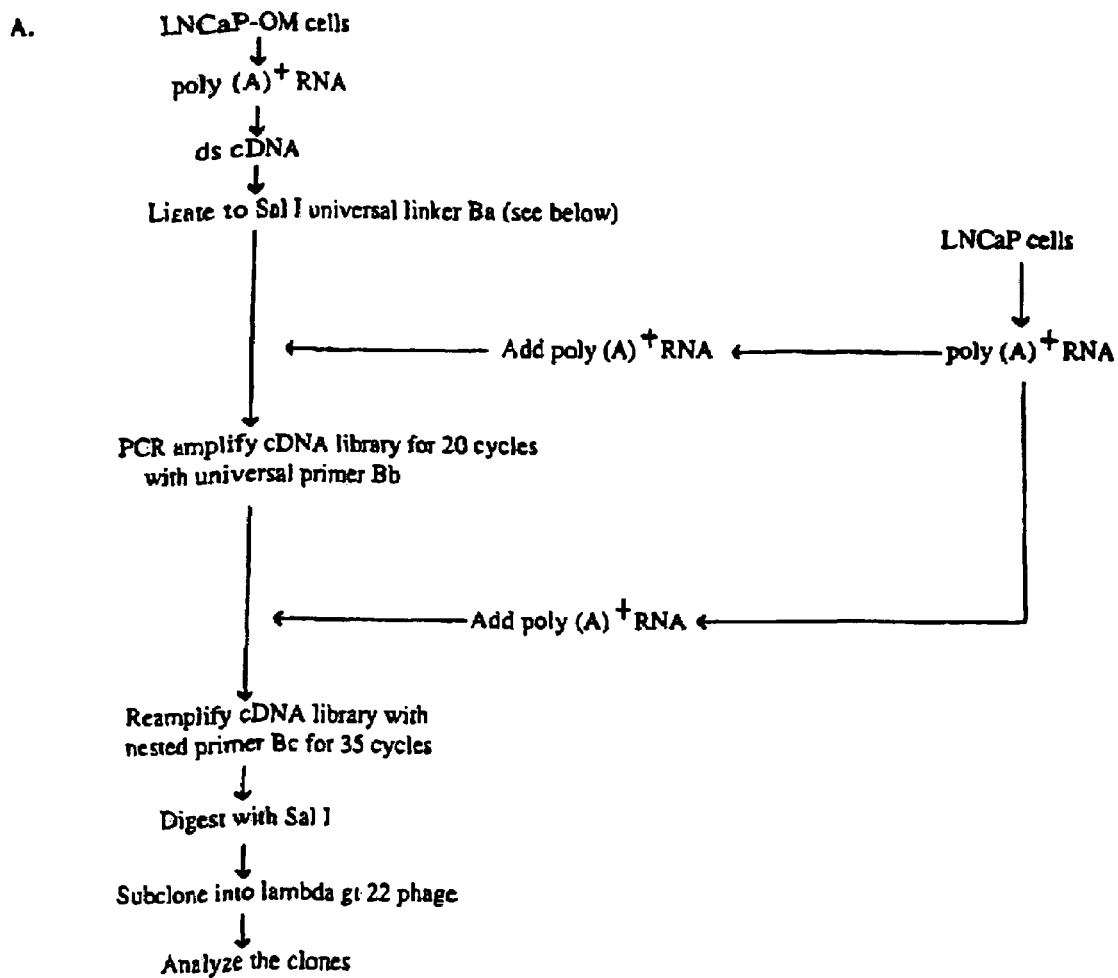

Hatakeyama et al., "JTB: A novel membrane protein gene at $1_q21$ rearranged in a jumping translocation," Oncogene 18:2085-2090, 1999.

Hubank and Schatz, "Identifying differences in mRNA expression by representational difference analysis of cDNA," Nucl. Acids Res. 22:5640-5648, 1994.

Isaacs et al., "The biology of hormone refractory prostate cancer," Urol. Clin. North Amer. 26:263-273, 1999.

Lalani et al., "Prostate cancer; the interface between pathology and basic scientific research," Semin. Cancer Biol. 8:53-59, 1997.

Lazar et al., "Transforming growth factor α: mutation of aspartic acid 47 and leucine 48 results in different biological activities," Mol. Cell. Biol. 8:1247-1252, 1988.

Liang and Pardee, "Differential display of eukaryotic messenger RNA by means of the polymerase chain reaction," Science 257:967-971, 1992.

Lin et al., Structure function relationships in glucagon: properties of highly purified des-his[1]-, monoiodo-, and [des-asn[28],thr[29]](homoserine lactone [27])-glucagon, Biochemistry 14:1559-1563, 1975.

Lisitsyn et al., "Cloning the differences between two complex genomes," Science 259:946-951, 1993.

Liu et al., "Identification of differentially expressed prostate genes: increased expression of transcription factor ETS-2 in prostate cancer," Prostate 30:145-153, 1997.

McClean et al., "Evidence of post-translational regulation of p-glycoprotein associated with the expression of a distinctive multiple drug-resistant phenotype in Chinese hamster ovary cells," Eur. J. Cancer 29A:2243-2248, 1993.

Platica et al., "PAR, a novel androgen regulated gene, ubiquitously expressed in normal and malignant cells," Int. J. Oncol. 16:1055-1061, 2000.

Platica et al., "PAR, a novel gene differentially regulated by androgens in hormone sensitive and resistant prostatic carcinoma cells," Abstract, International Symposium on Biology of Prostate Growth, Bethesda, MD, Mar. 1998.

Platica et al., "PAR, a novel ubiquitously expressed gene is upregulated in breast and prostate malignant cells," Abstract, American Association for Cancer Research Annual Meeting, Philadelphia, PA, Apr. 1999.

Platica et al., "LNCaP, A new androgen-resistant prostate cancer subline," In Vitro Cell. Develop. Biol. (Animal) 33:147-149, 1997.

Platica et al., "The cDNA sequence and the deduced amino acid sequence of human transcobalamin II show homology with rat intrinsic factor and human transcobalamin I," J. Biol. Chem. 266:7860-7863, 1991.

Platica et al., "Isolation of the complementary DNA for human transcobolamin II," Proc. Soc. Exp. Biol. Med. 192:95-97, 1989.

Regec et al., "The cloning and characterization of the human transcobalamin II gene," Blood 85:2711-2719, 1995.

Shantz et al., "Translational regulation of ornithine decarboxylase and other enzymes of the polyamine pathway," Int. J. Biochem. Cell Biol. 31:107-122, 1999.

Schalken et al., "Down modulation of fibronectin messenger RNA in metastasizing rat prostatic cancer cells revealed by differential hybridization analysis," Cancer Res. 48:2042-2046, 1988.

Schwartz et al., "A superactive insulin: [B10-Aspartic acid]insulin(human)," Proc. Natl. Acad. Sci. USA 84:6408-6411, 1987.

Stenman et al., "Accurate determination of relative messenger RNA levels by RT-PCR: the increasing focus on functional genomics spurs new techniques for accurately quantitating differences in mRNA levels," Nature Biotechnol. 17:720-722, 1999.

Sun et al., "Human prostatic carcinoma oncogene PTI-1 is expressed in human tumor cell lines and prostate carcinoma patient blood samples," Cancer Res. 57:18-23, 1997.

Wang et al., "Two differentially expressed genes in normal human prostate tissue and in carcinoma," Cancer Res. 56:3634-3637, 1996.

Yang et al., "Identification of genes expressed differentially by LNCaP or PC-3 prostate cancer cell lines," Cancer Res., 58:3732-3735, 1998.

* cited by examiner

```
  2 CGACGCGGAAGACTATAAGCCCCAGCGGGCGACGACCGAACGCCCCCGGGAACACCGGGC    61

62 CCCGAGCTCGGTCCCGCGCCCGAGGATCCTCCACGGGGCTAGATGGCTGCGTCGGGGGCG   121

122 GGAGCGGAGGTGAGCGGGCGCTAGGGCCGCGAGCCCCGCCGGCCCTTCCTCCAGCGCCC    181

182 TGCGGACCCCGCAGAAGGCGCTCGCCTCCCTAGCCCGCAAAAACATATCGATTTTTCTCG   241

242 CTGTGGCAACGGGGACGTCCTGATAGATCCTCTGCTCCAATAGGCAACTCCGGCCTTCCC   301

302 TGCCCTGACCTGGAACCTCTGGGAGGGCTGCAGAGTAAGTGCCGCCTCTGCGCTCCGACG   361

362 GAGGCACGAGGCCTGTGGAGTAGGTCCCTCTGTTCCGACAGGTGCGACACTTGGCGCTCC   421

422 ATGCTTGCGGGTGCCGGGAGGCCTGGCCTCCCCCAGGGCCGCCACCTCTGCTGGTTGCTC   481
  1  M  L  A  G  A  G  R  P  G  L  P  Q  G  R  H  L  C  W  L  L   20

482 TGTGCTTTCACCTTAAAGCTCTGCCAAGCAGAGGCTCCCGTGCAGGAAGAGAAGCTGTCA   541
 21  C  A  F  T  L  K  L  C  Q  A  E  A  P  V  Q  E  E  K  L  S    40

542 GCAAGCACCTCAAATTTGCCATGCTGGCTGGTGGAAGAGTTTGTGGTAGCAGAAGAGTGC   601
 41  A  S  T  S  N  L  P  C  W  L  V  E  E  F  V  V  A  E  E  C   60

602 TCTCCATGCTCTAATTTCCGGGCTAAAACTACCCCTGAGTGTGGTCCCACAGGATATGTA   661
 61  S  P  C  S  N  F  R  A  K  T  T  P  E  C  G  P  T  G  Y  V   80

662 GAGAAAATCACATGCAGCTCATCTAAGAGAAATGAGTTCAAAAGCTGCCGCTCAGCTTTG   721
 81  E  K  I  T  C  S  S  S  K  R  N  E  F  K  S  C  R  S  A  L   100

722 ATGGAACAACGCTTATTTTGGAAGTTCGAAGGGGCTGTCGTGTGTGTGGCCCTGATCTTC   781
101  M  E  Q  R  L  F  W  K  F  E  G  A  V  V  C  V  A  L  I  F   120

782 GCTTGTCTTGTCATCATTCGTCAGCGACAATTGGACAGAAAGGCTCTGGAAAAGGTCCGG   841
121  A  C  L  V  I  I  R  Q  R  Q  L  D  R  K  A  L  E  K  V  R   140

842 AAGCAAATCGAGTCCATATAGCTACATTCCACCCTTGTATCCTGGGTCTTAGAGACCCTA   901
141  K  Q  I  E  S  I  *                                          146

902 TCTCAGACAGTGAAAGTGAAATGGACTGATTTGCACTCTTGGTTCTTTGGAGCCTTGTGG   961

962 TGGAATCCCCTTTTCCCCATCTTCTTCTTTCAGATCATTAATGAGCAGAATAAAAAGAGT  1021

1022 AAAATGGTAAAAAAAAA                                             1038
```

FIGURE 2

PAR, A NOVEL MARKER GENE FOR BREAST AND PROSTATE CANCERS

This application is a continuation of U.S. patent application Ser. No. 09/467,262, filed Dec. 20, 1999 now abandoned.

1. INTRODUCTION

The present invention relates to a gene selectively expressed in malignant cells and associated with the development of androgen resistance in prostate cancer. Levels of the gene, termed "PAR" (for Prostate Androgen Regulated), its RNA transcript, and its protein product are all present at increased levels in malignant cells, such as breast cancer and prostate cancer cells. The present invention provides for PAR nucleic acid molecules and proteins, for antibodies that specifically bind to PAR proteins, and to methods for diagnosing and treating cancers that utilize such molecules.

2. BACKGROUND OF THE INVENTION

Androgen ablation, the main form of therapy for metastatic prostate cancer, can produce significant palliation of symptoms in a majority of patients. The success of this approach depends on the ability of the prostate cancer cells to respond to androgens (and hence, be controlled by androgen antagonists). However, after a variable period of time, in virtually all instances the cancer cells become resistant to androgens and therapeutic anti-androgenic agents. As a result, patients become refractory to therapy and experience a rapid disease progression and death (Gittes, 1991, N. Engl. J. Med. 324: 236-245; Crawford et al., 1995, J. Clin. Endocrinol. Metabolism 80: 1062-1078). Despite intense investigation, the molecular basis for malignant transformation of prostatic epithelial cells and their transition to androgen resistance is still poorly understood (Lalani et al., 1997, Semin. Cancer Biol. 8: 53-9; Isaacs, et al., 1999, Urol Clin. North Am. 26: 263-73).

A search for genes differentially expressed in androgen dependent and independent prostatic carcinoma cells has been an avenue extensively investigated. During the past few years several novel genes like NPG-1 (Yang et al., 1998, Cancer Res. 58: 3732-3735), JC19, GC79 (Chang et al., 1997, Cancer Res. 57:4075-4081) and others (Blok et al., 1995, Prostate 26: 213-224; Chuaqui et al., 1997, Urology 50: 302-307; Geck et al., 1997, J. Steroid Mol. Biol. 63: 211-218) have been shown to be differentially expressed in androgen sensitive prostate cancer cells in comparison with the hormone refractory tumors. In addition, known genes like vimentin (Bussemarkers et al., 1992, Biochem. Biophys. Res. Commun. 182: 1254-1259), fibronectin (Schalken et al., 1988, Cancer Res. 48: 2042-2046), epithelial tropomyosin and cytochrome c oxidase (Wang et al., 1996, Cancer Res. 56: 3634-3637), the ETS-2 and SEF-2 factors (Liu et al., 1997, Prostate 30: 145-153) and PTI-1 gene (Sun et al., 1997, Cancer Res. 57: 18-23) have been found to be expressed at different levels in hormone sensitive and resistant prostate cancers. The role of these genes in malignant transformation and the transition to androgen resistance is not yet established.

Using a modified representational difference analysis (RDA) (Lisitsyn et al., 1993, Science 259: 946-951) six differentially expressed genes have been isolated from LNCaP-OM, an androgen resistant subline developed from the original LNCaP line (Platica et al., 1997, In Vitro Cellular and Developmental Biology, (Animal) 33: 147-149).

The present invention relates to the isolation, complete sequencing and characterization of one of these genes, termed "PAR" for "Prostatic Androgen Regulated", and to the discovery that PAR expression is associated with malignant transformation. The National Institute of Genetics in Japan has reported that on Oct. 9, 1998, a nucleic acid sequence deposited by Hatakeyama et al. as accession number AB016492, "hjTB, a novel membrane protein at 1q21 rearranged in a jumping translocation", was released by the DNA Data Bank of Japan ("DDBJ"). This sequence is 98% homologous to a substantial portion of the nucleotide sequence of PAR cDNA set forth in FIG. 2 and SEQ ID NO:1, but no other information regarding the gene was provided by Hatakeyama et al.

3. SUMMARY OF THE INVENTION

The present invention is based, at least in part, on the discovery of a gene termed "PAR" which was isolated from an androgen resistant prostate cancer cell line by a modified representational difference analysis. While PAR was found to be expressed in all 29 normal tissues studied, it was overexpressed in 16 out of the 24 human malignant tissues tested, including, in particular, breast cancer and prostate cancer cells. PAR is down regulated by androgens in human androgen-sensitive prostate cancer cells, but not in hormone-resistant cells, indicating that its expression is linked to the emergence of the androgen-resistant malignant phenotype. Further, it was discovered that the PAR gene itself is amplified in malignant cells, that increased PAR expression induces cell proliferation, and that blocking PAR expression inhibits the proliferation of malignant cells.

In a first set of embodiments, the present invention provides for PAR nucleic acids, including DNA comprising a nucleotide sequence as set forth in FIG. 2 (SEQ ID NO:1) and other DNA and RNA molecules which encode a protein having an amino acid sequence as set forth in FIG. 2 (SEQ ID NO:2), such as, for example, the coding region of SEQ ID NO:1, which is designated SEQ ID NO:9, as well as nucleic acids which hybridize thereto under stringent conditions and which encode a functional PAR protein. Recombinant DNA containing the PAR cDNA, cloned in a pCMV-script vector, was deposited with the American Type Culture Collection, 10801 University Blvd, Manassa, Va. 20110-2209 on Dec. 3, 1999, and assigned accession number PTA-1012.

In a second set of embodiments, the present invention provides for PAR proteins, including proteins comprising an amino acid sequence as set forth in FIG. 2 (SEQ ID NO:2).

In a third set of embodiments, the present invention provides for antibodies that recognize a PAR protein.

In a third set of embodiments, the present invention provides for methods of diagnosing malignancy that include detecting increased amounts of PAR nucleic acids or proteins in cells. Because it has been discovered that both PAR DNA and RNA levels are increased in transformed cells, these methods may quantitate either species of nucleic acid. Where the diagnostic method involves the measurement of protein levels, antibody specifically directed toward a PAR protein may be utilized.

In a fourth set of embodiments, the present invention provides for methods of determining the progression of malignancy in a subject, where an increase in the amount of PAR nucleic acid or protein may be positively correlated with advancement of disease.

In a fifth set of embodiments, the present invention provides for methods of treating a subject suffering from a malignancy which comprise decreasing the amount of PAR in the subject, for example by decreasing the level of PAR nucleic acid or protein (e.g. by the introduction of antisense PAR nucleic acid).

In a sixth set of embodiments, the PAR molecules of the invention may be used to produce model systems for the study of carcinogenesis and malignant progression and for the identification of therapeutic agents that intervene in such processes. A transgenic animal carrying a transgene encoding PAR is an example of one such model system.

4. DESCRIPTION OF THE FIGURES

FIG. 1A-1B. Subtraction method. A. Experimental strategy to identify the genes expressed selectively in androgen resistant (LNCaP-OM) versus androgen sensitive (LNCaP) prostatic cancer cells. B. The universal linker Ba (SEQ ID NOs: 6 and 7) and the two nested PCR primers Bb (SEQ ID NO: 11) and Bc (SEQ ID NO: 8) for subtraction of cDNA library as shown in A.

FIG. 2. PAR cDNA sequence (SEQ ID NO:1) and its deduced amino acid encoding sequence (SEQ ID NO:2). A sense primer (SEQ ID NO:3) and anti-sense primer (SEQ ID NO:4) for amplification of a PAR-specific probe (SEQ ID NO:5) are represented, respectively, by overlining of asterisks (SEQ ID NO:3) and dashes (SEQ ID NO:4), with the sequence between represented by a solid line, with the entire sequence bounded by SEQ ID NO:3 and SEQ ID NO:4 being SEQ ID NO:5.

FIG. 3A-B. PAR expression in RNA from various normal human tissues as determined by Northern blot analysis. A) normal human esophagus, stomach, intestine, colon, uterus, placenta, bladder and adipose tissue. B) normal human white blood cells, colon, small bowel, ovary, testis, prostate, thymus and spleen. 2 µg poly (A)$^+$ RNA from each tissue was hybridized successively to PAR and 28S rRNA probes.

Figure 4:
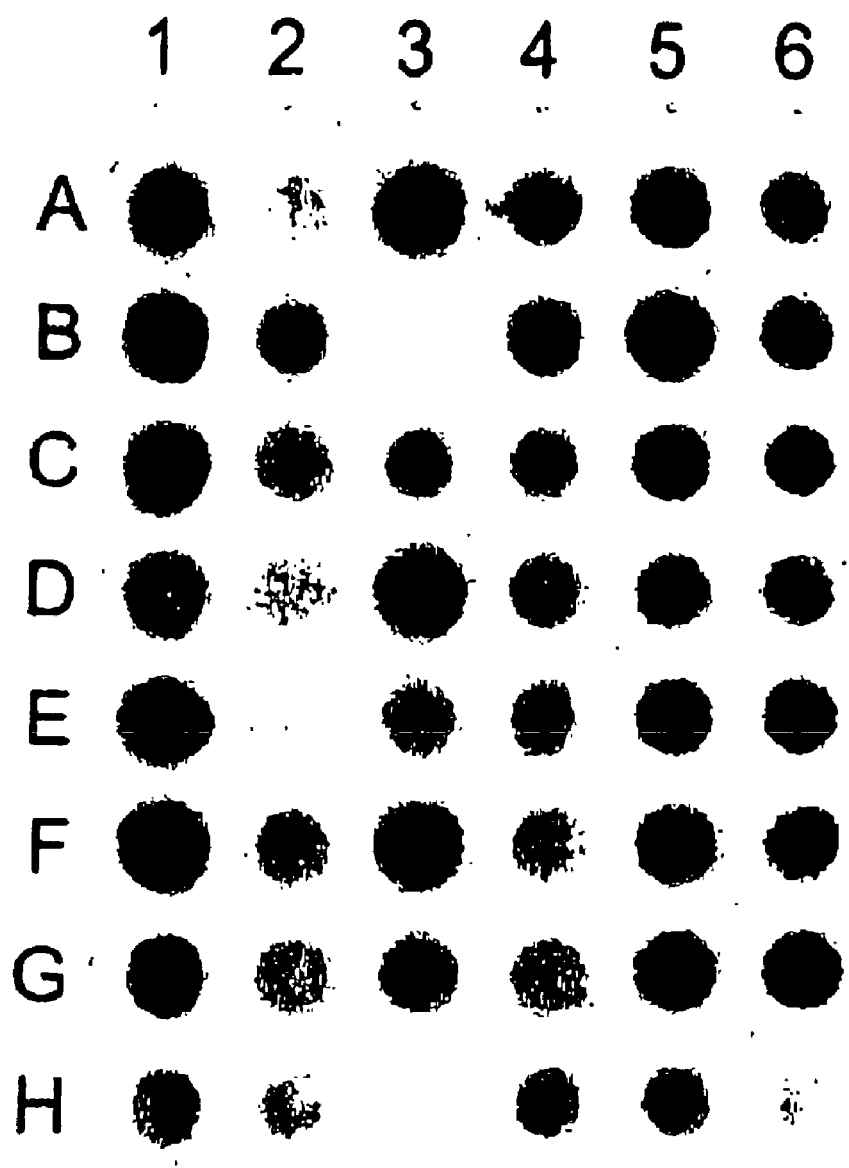

FIG. 4. Multiple total RNA dot blot from malignant and normal tissues hybridized to PAR probe. Rows A1-6: brain, gallbladder, ovary; Rows B1-6: lung, pancreas, breast; Rows C1-6 esophagus, parotid, Fallopian tubes; Rows D1-6: stomach, kidney, uterus; Rows E1-6: duodenum, ureter, thyroid; Rows F1-6: colon, bladder, adrenal; Rows G1-6: rectum, prostate, thymus; Rows H1-6: liver, testis, non-Hodgkin's lymphoma. Each row contains malignant tissue (odd numbers) and normal counterpart tissue (even numbers). 2 µg total RNA prepared from 24 malignant tissues and their normal counterparts were blotted to a positively charges nylon membrane, crosslinked, and fixed by baking, for 3 hours. Then, the blot was hybridized successively to PAR and 28S rRNA probes.

FIG. 5A-C. Expression of PAR in prostate cancer cells. (A) Northern blot prepared from total RNA of normal prostate tissue (a), and prostate cancer cell lines DU145 (b), LNCaP-OM (c), LNCaP (d) and PC3 (e) hybridized to PAR probe (A) and 28S rRNA probe (B); Densitometric reading (%) of normalized PAR expression as determined from Northern blot in A, B (C).

FIG. 6A-C. PAR expression in breast tumor cells. Northern blot prepared from total RNA of normal breast tissue (a), and MCF-7 (b) and T47D (c) breast cancer cell lines hybridized to PAR probe (A) and 28S RNA probe (B); Densitometric reading (%) of normalized PAR expression as determined from Northern blot in A, B (C).

FIG. 7A-B. Differential expression of PAR in normal and malignant breast tissues. A) Northern blot prepared from total RNA from breast tumor tissues (a1, b1, c1, and d1) and their normal counterparts (a2, b2, c2, and d2) from 4 different patients (a, b, c, and d) hybridized to PAR probe. B) Densitometric reading (%) of PAR expression as determined by Northern blot analysis from (A).

FIG. 8A-C. Androgen regulation of PAR expression in androgen sensitive LNCaP cells. Northern blot prepared from total RNA from LNCaP cells grown in cs-FCS (a), cs-FCS+ $10^{-10}$ M R1881 (b) and cs-FCS $10^{-9}$ M R1881 (c) hybridized to PAR probe (A) and 28S r RNA probe (B). Densitometric reading (%) of normalized PAR expression as determined from Northern blot+(A, B) (C).

5. DETAILED DESCRIPTION OF THE INVENTION

For clarity of presentation and not by way of limitation, the detailed description of the invention is divided into the following subsections:

(i) PAR nucleic acids and proteins;
(ii) Anti-PAR antibodies;
(iii) methods of diagnosis;
(iv) methods of treatment; and
(v) model systems of disease.

5.1 Par Nucleic Acids and Proteins

The present invention relates to a PAR gene, RNA transcribed from a PAR gene or any cDNA or antisense counterparts thereof. The term "PAR gene", as used herein, refers to the PAR gene having a nucleic acid sequence as set forth in FIG. 2 (SEQ ID NO:1), a nucleic acid sequence as set forth in Accession No. AF115850 of the GenBank database, and the nucleic acid sequence as contained in the PAR-encoding cDNA deposited with the American Type Culture Collection, 10801 University Boulevard, Manassas, Va. 20110-2209 and assigned accession number PTA-1012, and alleles in humans, and homologs in other species, thereof which are at least about 90 percent, and preferably about 95 percent, homologous to the human PAR gene set forth in FIG. 2 and SEQ ID NO:1 (homology determined by MACVECTOR, Blast Search Algorithm (Netscape Navigator, 3.01)), and/or which hybridize to the human PAR gene under stringent hybridization and wash conditions, such as hybridization in 50 percent formamide, 5×SSPE, 2× Denhardt's, 0.5 percent SDS, 100 µg/ml salmon sperm DNA, at 42° C.; and washes in 0.2×SSC, 0.1 percent SDS at 50° C. Nucleic acids defined by hybridization encode a functional PAR protein. The term "functional PAR protein", as defined herein, refers to a protein having at least one of the following features: a size of between 140-170 amino acid residues, expression at increased levels in malignant relative to nonmalignant cells, expression at increased levels in androgen-resistant as compared to androgen-sensitive prostate cancer cells, and the ability to stimulate cell proliferation.

The present invention also provides for nucleic acid molecules which hybridize to a PAR gene under stringent conditions as set forth above and encode, directly or indirectly, a functional PAR protein, including complementary DNA and RNA molecules, including mRNA transcripts of the PAR gene as well as nucleic acid molecules which are "antisense", that is to say, complementary to a mRNA transcript of the PAR gene. Preferably, the conditions for hybridization and washing are as follows: hybridization in 50 percent formamide, 5×SSC, 2× Denhardt's, 0.5 percent SDS, 100 µg/ml salmon sperm DNA at 42° C., and washes is 0.2 SSC, 0.1 percent SDS at 50° C.

The present invention still further provides for nucleic acid molecules that encode a protein having an amino acid sequence as set forth in FIG. 2 (SEQ ID NO:2), such as, for example, the coding region of SEQ ID NO:1, designated herein as SEQ ID NO:9, and to nucleic acid molecules which hybridize thereto under stringent conditions and that encode a functional PAR protein.

In a specific nonlimiting embodiment, the present invention provides for a nucleic acid molecule that is a fragment from the initial PAR clone having a nucleotide sequence as set forth in FIG. 2 (SEQ ID NO:5). This fragment may be used as a probe to detect and/or measure PAR expression, and may be produced by PCR amplification using the primers 5'-GCCACCTCTGCTGGTTGCTCTG-3' (SEQ ID NO:3; sense) and 5'-CCAGGATACAAGGGTGGAATGT-3' (SEQ ID NO:4; antisense).

The present invention still further provides for purified and isolated PAR proteins. The term "PAR protein", as used herein, includes human PAR protein, having an amino acid sequence as set forth in FIG. 2 (SEQ ID NO:2) and proteins which are at least 90 percent, and preferably 95 percent, homologous to human PAR protein as determined by MACVECTOR and the Blast Search Algorithm. In a specific embodiment, the PAR protein is a 145-147, preferably 146 amino acid protein having a sequence as set forth in FIG. 2 (SEQ ID NO:2).

The PAR gene or a corresponding cDNA or RNA may be incorporated into any suitable cloning or expression vector, operably linked to appropriate control elements (e.g., promoter/enhancer elements, ribosomal binding sites, polyadenylation sites, termination sites, etc.). Examples of such vectors include, but are not limited to, herpes simplex viral based vectors such as pHSV1 (Geller et al., 1990, Proc. Natl. Acad. Sci. U.S.A. 87:8950-8954); retroviral vectors such as MFG (Jaffee et al., 1993, Cancer Res. 53:2221-2226), and in particular Moloney retroviral vectors such as LN, LNSX, LNCX, LXSN (Miller and Rosman, 1989, Biotechniques 7:980-989); vaccinia viral vectors such as MVA (Sutter and Moss, 1992, Proc. Natl. Acad. Sci. U.S.A. 89:10847-10851); adenovirus vectors such as pJM17 (Ali et al., 1994, Gene Therapy 1:367-384; Berker, 1988, Biotechniques 6:616-624; Wand and Finer, 1996, Nature Medicine 2:714-716); adeno-associated virus vectors such as AAV/neo (Mura-Cacho et al., 1992, J. Immunother. 11:231-237); lentivirus vectors (Zufferey et al., 1997, Nature Biotechnology 15:871-875); and plasmid vectors such as pCDNA3 and pCDNA1 (InVitrogen), pET 11a, pET3a, pET11d, pET3d, pET22d, pET12a and pET28a (Novagen); plasmid AH5 (which contains the SV40 origin and the adenovirus major late promoter), pRC/CMV (InVitrogen), pCMU II (Paabo et al., 1986, EMBO J. 5:1921-1927), pZipNeo SV (Cepko et al., 1984, Cell 37:1053-1062), pSRα (DNAX, Palo Alto, Calif.) and pBK-CMV, pSPTg.T2FpAXK and pSPTg.2FXK (Schaleger et al., 1997, Proc. Natl. Acad. Sci. U.S.A. 94:3058-3063).

In specific, nonlimiting embodiments of the invention, a PAR gene or a corresponding cDNA or RNA may be incorporated into an expression vector as part of a fusion protein or as a dicistronic expression cassette together with a second gene. For example, such a gene may be a reporter gene (e.g., human placental alkaline phosphatase, luciferase, β-galactosidase, etc.).

In other specific, nonlimiting embodiments of the invention, an expression vector or other PAR nucleic acid may comprise a PAR gene (or a corresponding cDNA or RNA) operably linked to a heterologous promoter (i.e., a promoter not found, in nature, linked to the PAR gene). The heterologous promoter may be a tissue specific promoter or an inducible promoter. For example, if the PAR nucleic acid is to be used as a transgene in a transgenic animal model for breast cancer, the PAR-encoding portion (e.g., the open reading frame indicated in FIG. 2) may be operably linked to a promoter that is selectively active in breast tissue. Likewise, if the PAR nucleic acid is to be used as a transgene in a transgenic animal model of prostate cancer, the PAR-encoding region may be operably linked to a promoter that is selectively active in prostate tissue. In alternative embodiments, the heterologous promoter may be an inducible promoter, such as the metallothionine promoter.

5.2 Anti-Par Antibodies

The present invention further provides for antibody molecules which specifically bind to a PAR protein. According to the invention, a PAR protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In specific embodiments, antibodies to human PAR protein are produced.

Various procedures known in the art may be used for the production of polyclonal antibodies which specifically bind to a PAR protein. In a particular embodiment, rabbit polyclonal antibodies to an epitope of a PAR protein having an amino acid sequence set forth in FIG. 2 (SEQ ID NO:2) may be obtained. For the production of antibody, various host animals can be immunized by injection with the native PAR protein, or a synthetic version, or derivative (e.g., fragment) thereof, including but not limited to rabbits, mice, rats, etc. Various adjuvants may be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a PAR protein, any technique which provides for the production of antibody molecules by continuous cell lines in culture may be used. Examples of such techniques include the hybridoma technique originally developed by Kohler and Milstein (1975, Nature 256:495-497), as well as the trioma technique, the human B-cell hybridoma technique (Kozbor et al., 1983, Immunology Today 4:72), and the EBV hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for PAR together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce PAR-specific single chain antibodies. An additional embodiment of the invention utilizes the techniques described for the construction of Fab expression libraries (Huse et al., 1989, Science 246:12751281) to allow rapid and easy identification of monoclonal Fab fragments with the desired specificity for PAR protein derivatives, or analogs.

Antibody fragments which contain the idiotype of the molecule can be generated by known techniques. For example, such fragments include but are not limited to: the F(abl), fragment which can be produced by pepsin digestion of the antibody molecule; the Fab' fragments which can be generated by reducing the disulfide bridges of the F(abl), fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a PAR protein, one may assay generated hybridomas for a product which binds to a PAR fragment containing such domain.

5.3 Methods of Diagnosis

The present invention provides a method for diagnosing a malignant disease in a subject comprising comparing the quantity of PAR gene or a PAR gene product (e.g., RNA or protein) in a cell or tissue from the subject with a comparable non-malignant control cell or tissue, where an increase in the quantity of PAR gene or a PAR gene product in the cell or tissue of the subject bears a positive correlation with the presence of malignancy.

In particular embodiments, the present invention provides for a method for diagnosing the presence of cancer in a subject, comprising (a) collecting a test sample from the subject, where the test sample contains cells; (b) measuring the amount of PAR-encoding RNA in the test sample; and (c) comparing the amount of PAR-encoding RNA measured in step (b) to the amount present in a corresponding normal sample; where the presence of a greater amount of PAR-encoding RNA in the test sample relative to the normal sample has a positive correlation with the presence of cancer in the subject. In preferred, nonlimiting embodiments, the cancer is prostate cancer or breast cancer. A test sample may be a tissue sample, a fluid sample (for example a body fluid, including a tumor exudate), or a collection of cells prepared from a tissue or fluid.

In particular embodiments, the RNA may be measured by (i) preparing RNA from the test sample; (ii) hybridizing the RNA with a nucleic acid molecule which hybridizes under stringent conditions to a nucleic acid molecule having a sequence as set forth in SEQ ID NO:1; and (iii) detecting the amount of hybridization that has occurred. In preferred embodiments, the RNA may be hybridized to a probe selected from the group consisting of a nucleic acid molecule having a nucleic acid sequence as set forth in SEQ ID NO:1 or SEQ ID NO:5 or portions thereof having a length of at least 5 nucleotides and preferably 25-75 nucleotides.

In other embodiments of the invention, the amount of PAR-encoding RNA may be measured by (i) preparing RNA from the test sample; (ii) preparing cDNA from the RNA; (iii) amplifying a PAR-specific fragment of the cDNA; and (iv) quantifying the amount of PAR-specific fragment generated. In one specific nonlimiting embodiment, the PAR-specific fragment of cDNA is amplified using a pair of nucleotide primers having nucleic acid sequences as set forth in SEQ ID NOS: 3 and 4.

In another embodiment, the present invention provides for a method for diagnosing the presence of cancer in a subject, comprising (a) collecting a test sample from the subject; (b) measuring the amount of PAR protein in the test sample; and (c) comparing the amount of PAR protein measured in step (b) to the amount present in a corresponding normal sample; where the presence of a greater amount of PAR protein in the test sample relative to the normal sample has a positive correlation with the presence of cancer in the subject. The test sample may be a tissue sample, a fluid sample (such as a blood sample, urine sample, cerebral spinal fluid sample, exudate sample, etc.) or a cell sample prepared from a tissue sample or a fluid sample. In preferred nonlimiting embodiments, the cancer may be prostate cancer or breast cancer. In particular nonlimiting embodiments of the invention, the amount of PAR protein may be measured using an antibody that specifically binds to a protein having the amino acid sequence as set forth in SEQ ID NO:2. For example, the antibody may be used in a Western blot assay, immunohistochemical assay, or an ELISA assay. As a specific nonlimiting example, binding of antibody to PAR protein may be detected using a detectably labeled secondary reagent.

According to additional embodiments, the present invention provides for a method for evaluating advancement in the stage of a cancer in a subject, comprising (a) collecting a first test sample, where the test sample contains cells, from the subject at a first point in time; (b) measuring the amount of PAR-encoding RNA in the first test sample; (c) collecting a second test sample, where the test sample contains cells, from the subject at a second later point in time; (d) measuring the amount of PAR-encoding RNA in the second test sample; and (e) comparing the amount of PAR-encoding RNA measured in step (b) to the amount of PAR-encoding RNA measured in step (d); where an increase in the amount of PAR-encoding RNA in the second test sample relative to the first test sample has a positive correlation with the advancement in the stage of the cancer in the subject. The sample may be a tissue sample or a cell-containing fluid sample or a cell sample prepared from a tissue or a fluid. In preferred, nonlimiting embodiments, the cancer may be prostate cancer or breast cancer. In particular examples, the amount of PAR-encoding RNA may be measured by (i) preparing RNA from the test sample; (ii) hybridizing the RNA with a nucleic acid molecule which hybridizes under stringent conditions to a nucleic acid molecule having a sequence as set forth in SEQ ID NO:1; and (iii) detecting the amount of hybridization that has occurred. Specifically, the amount of PAR-encoding RNA may be measured by (i) preparing RNA from the test sample; (ii) hybridizing the RNA to a probe selected from the group consisting of a nucleic acid molecule having a nucleic acid sequence as set forth in SEQ ID NO:1 or SEQ ID NO:5 and a portion thereof having a length of at least 5 nucleotides; and (iii) detecting the amount of hybridization that has occurred. Alternatively, the amount of PAR-encoding RNA may be measured by (i) preparing RNA from the test sample; (ii) preparing cDNA from the RNA; (iii) amplifying a PAR-specific fragment of the cDNA; and (iv) quantifying the amount of PAR-specific fragment generated. In a specific, nonlimiting example, the PAR-specific fragment of cDNA may be amplified using a pair of nucleotide primers having nucleic acid sequences as set forth in SEQ ID NOS:3 and 4. Other methods for measuring the amount of RNA, known in the art, may also be used.

In related embodiments, the invention provides for a method for evaluating advancement in the stage of a cancer in a subject, comprising (a) collecting a first test sample from the subject at a first point in time; (b) measuring the amount of PAR protein in the first test sample; (c) collecting a second test sample from the subject at a second later point in time; (d) measuring the amount of PAR protein in the second test sample; and (e) comparing the amount of PAR protein measured in step (b) to the amount of PAR protein measured in step (d); where an increase in the amount of PAR protein in the second test sample relative to the first test sample has a positive correlation with the advancement in the stage of the cancer in the subject. The test sample may be a tissue sample, a fluid sample (e.g. a blood sample, a urine sample, a cerebrospinal fluid sample, or an exudate, etc.) or a cell sample prepared from a tissue sample or a fluid sample. In preferred embodiments, the cancer is prostate cancer or breast cancer. In particular nonlimiting embodiments, the amount of PAR protein may be measured using an antibody that specifically binds to a protein having the amino acid sequence as set forth in SEQ ID NO:2. For example, the antibody may be used in a Western blot, immunohistochemical, or ELISA assay. In certain embodiments, binding of antibody to PAR protein may be detected using a detectably labeled secondary reagent.

In still further embodiments, the present invention provides for a method for diagnosing the presence of cancer in a subject, comprising (a) collecting a test sample from the subject, where the test sample comprises cells; (b) measuring the amount of deoxyribonucleic acid which hybridizes, under stringent conditions, to a nucleic acid molecule having a nucleic acid sequence as set forth in SEQ ID NO:1 in the test sample; and (c) comparing the amount of deoxyribonucleic acid measured in step (b) to the amount present in a corresponding normal sample; where an increase in the amount of deoxyribonucleic acid measured in the test sample relative to the normal sample has a positive correlation with the presence of cancer in the subject. In preferred nonlimiting embodiments, the cancer is breast cancer or prostate cancer.

5.4 Methods of Treatment

The present invention provides for methods for treating proliferative disorders, including but not limited to neoplasms and malignancies, comprising administering, to a subject in need of such treatment, an effective amount of a PAR protein antagonist. The term "effective amount" is defined herein as meaning an amount that will decrease cell proliferation by at least about 10 percent, preferably at least about 25 percent, and more preferably by at least about 50 percent. The term "PAR protein antagonist" is defined as a molecule which will produce the effect of decreasing the amount of available PAR protein. For example, an anti-sense RNA is a PAR protein antagonist. The malignancy may be, but is not limited to, breast cancer or prostate cancer.

In related embodiments, the present invention provides for methods of inhibiting the proliferation of a cell comprising exposing the cell to an effective amount of a PAR protein antagonist. The terms "effective amount" and "PAR protein antagonist" are as set forth above. The cell may be a cancer cell, such as, but not limited to, a breast cancer cell or a prostate cancer cell. Alternatively, the cell may be a nonmalignant proliferative cell, for example, but not limited to, a vascular endothelial cell.

The present invention also provides for a method of inducing proliferation of a cell comprising exposing the cell to an effective amount of a PAR protein. The term "effective amount" is defined herein as an amount that increases proliferation of the cell by at least about 25 percent, preferably by at least about 50 percent. The PAR protein may be administered directly or indirectly, for example by introducing, into the cell, a nucleic acid encoding the PAR protein. For example, it may be desirable to introduce a PAR gene, operably linked to an inducible promoter, in a cell that is desirably propagated. In a specific embodiment, if a cell is collected from an individual with the intention that the cell would be proliferated in vitro and then re-introduced into the individual, to reconstitute a tissue or organ or to provide immunity, it may be desirable to expand the number of such cells as much and as quickly as possible. Under such circumstances, it may be desirable to incorporate a PAR gene under the control of an inducible promoter, such that the inducer may be supplied in vitro to boost cell proliferation, but would be constitutively absent in vivo.

5.5 Model Systems for Disease

In still further embodiments, the present invention provides for model systems for disease. Such model systems may be comprised of cell cultures or tissue cultures or may be in the form of a transgenic animal carrying, as a transgene, a PAR gene.

For example, the present invention provides for a cell culture or a tissue culture comprising cells carrying an introduced PAR gene, where the level of PAR gene expression, including the expression of endogenous and introduced PAR genes, is greater than that found in comparable cells lacking the introduced PAR gene ("control cells"). The increase in PAR gene expression may be at least 10 percent, preferably at least 25 percent, and more preferably at least 50 percent greater than that found in control cells. In particular embodiments, the introduced PAR gene may be operably linked to a heterologous promoter. The heterologous promoter may be tissue specific or inducible or may be cell cycle specific. Such a cell culture or tissue culture may be used as a model for undesirable cell proliferation and/or for a malignancy. For example, introducing a PAR gene into a breast cancer cell line, such that levels of the PAR gene are increased, may produce a model for a more malignant form of breast cancer than that represented by the parental breast cancer cell line. Similarly, introducing a PAR gene into a prostate cancer cell line, such that levels of PAR are increased, may produce a model for a more malignant form of prostate cancer than that represented by the parental cell line, where the genetically engineered cell may be androgen-resistant.

In analogous embodiments, the present invention provides for transgenic animals carrying, as a transgene, a PAR gene. The PAR gene may be operably linked to its own promoter or a heterologous promoter. As one specific example, a transgenic animal may be produced carrying a transgene which comprises a PAR gene under the control of a promoter selectively expressed in breast or prostate cells. Such animals may serve as models for breast cancer or prostate cancer, respectively.

In the foregoing embodiments, the PAR gene may be the human PAR gene or may be the PAR gene of another species, such as (but not limited to) the same species as the cell, tissue, or animal into which it is introduced.

The cell cultures, tissue cultures, and transgenic animals described above may be used as model systems for the study of proliferative diseases and also for the identification of agents that are agonists or antagonists of PAR activity. As a specific, nonlimiting example, a cell line carrying an introduced PAR gene and which overexpresses PAR may be expected to proliferate more than a cell lacking the introduced PAR gene. If cells from this line are exposed to a test agent, and their proliferation decreases, the test agent may be an antagonist of PAR. If, alternatively, the proliferation rate increases, the agent may be an agonist of PAR. Similar experiments may be performed with tissue cultures and with transgenic animals.

6. EXAMPLE

Par, a Novel Gene Isolated from Human Androgen Resistant Prostate Cancer Cells, Differentially Expressed in Normal and Malignant Cells

6.1 Materials and Methods

6.1.1 Cell Lines and Tissue Culture Conditions

Human prostatic cancer cell lines LNCaP, DU 145 and PC3, as well as human breast cancer cell lines MCF-7 and T47 D were obtained from the American Type Culture Collection. The androgen resistant prostatic cell line LNCaP-OM was developed in our laboratory (Platica et al., 1997, In Vitro Cellular and Developmental Biology, (Animal) 33: 147-149). All cells were grown in RPMI 1640 medium supplemented with 10% FCS, 10 IU penicillin/ml and 50 µg streptomycin/ml, at 37° C. in a humidified atmosphere containing 5% $CO_2$ unless otherwise indicated.

6.1.2 Subtraction Method

The subtraction method used in this study is shown in FIG. 1A.

The cDNA library from the androgen resistant LNCaP-OM cells was prepared using a kit and the protocol from Gibco BRL (Grand Island, N.Y.). $^{32}P$ dCTP was incorporated in cDNA to facilitate monitoring. To generate clones of a size amplifiable by PCR the cDNA was divided in 3 aliquots; two aliquots were digested with the frequently cutting endonucleases Hae III or Alu I, and the third one was left unprocessed. Each aliquot was separated on Sepharose 6B and 10 µl from each fraction were subjected to electrophoresis in 1.2% agarose. The fractions containing cDNA fragments of 0.3-2 kb were collected and pooled. Equal amounts of radioactive material from each aliquot were pooled, made blunt ended, and ligated to the universal linker Ba (SEQ ID NOS:6 and 10, FIG. 1B). After removal of the free linkers, 50 ng of cDNA were mixed with 2.5 µg of poly $(A)^+$ RNA extracted from LNCaP cells and PCR amplified with the primer Bb (SEQ ID NO:7, FIG. 1B). The conditions of amplification consisted of Taq polymerase buffer (Stratagene, La Jolla, Calif.), 200 pmol dNTP, 100 pmol PCR primer and 5 units Taq polymerase in 50 µl volume. Cycling conditions were denaturation at 95° C. for 15 minutes, annealing at 58° C. for 15 minutes and extension at 72° C. for 2 minutes, for the first cycle, followed by denaturation at 95° C. for 30 seconds, annealing at 58° C. for 30 seconds, and extension at 72° C. for 2 minutes, for 20 cycles with a final extension at 72° C. for 7 minutes. PCR amplification was performed in a Perkin Elmer GeneAmp PCR system 2400. After removing the primers and RNA, the cDNA was reamplified in the presence of 5 µg poly $(A)^+$ RNA from LNCaP cells and 100 pmol of nested PCR primer Bc (SEQ ID NO:8), for 35 cycles in the same cycling conditions. The PCR product was digested with Sal I, purified of linkers and ligated to λ gt22 Sal I arms (Gibco BRL). After cloning the subtracted cDNA in λ gt22 vector, six plaques were randomly selected and amplified, and then, phage DNA prepared. The inserts were obtained by amplification of phage DNA clones with λ gt11 forward and reverse primers. Dot blots prepared from 5 µg total RNA extracted from LNCaP and LNCaP-OM cells were hybridized to each radioactive inserts. When necessary, phage clones were sequenced with λ gt11 primers.

6.1.3 Isolation and Sequencing of the Full Length Par cDNA

The initial PAR clone contained a 690 bp insert including the poly A tail.

To isolate the complete PAR gene, the full length cDNA sequences prepared for subtraction from androgen resistant LNCaP-OM cells were cloned into λ gt22 vector. The library was screened with the labeled PAR clone insert. Eight positive clones were identified and plaque purified by second and third screenings, as previously described (Platica et al., 1991, J. Biol. Chem. 266: 7860-7863). The clone with the largest insert containing the PAR sequence was subcloned in the Bluescript plasmid and sequenced several times in forward and reverse orientation in an ABI Prism 373 with XL upgrade, using 6 extension primers selected with OLIGO primer analysis software, version 5.0 (NBI/Genovus, Inc. Plymouth, Minn.). This clone had 954 bp.

For mapping the transcription start site of PAR mRNA the 5' RACE assay was used as described in Regec et al. (1995, Blood 85: 2711-2719) with a kit and the protocol from Gibco BRL. Three antisense primers were selected from the 5' extremity of the PAR cDNA sequence. The cDNA was synthesized from one microgram total RNA extracted from PC3 cells with the superscript II reverse transcriptase and the antisense primer located 320 bp downstream from the 5' end of PAR cDNA. After the addition of an oligo dC tail at the 3' cDNA end with terminal deoxynucleotidyltransferase, the product was PCR amplified using abridged anchor primer (AAP) from the kit and a primer located 280 nucleotides from PAR 5' end, under the cycling conditions indicated by the manufacturer. The amplification product was reamplified with the third antisense primer located 190 nucleotides of the 5' extremity AAP. A 220 bp unique fragment was obtained which was purified and sequenced with the third antisense primer.

6.1.4 Northern Blot Analysis

Two multiple tissue Northern blots, one from Clontech Laboratories, Inc., (Palo Alto, Calif.) and one from Invitrogen Corp. (San Diego, Calif.) were hybridized to the PAR probe. The blots were prepared by electrophoresis in a 1.2% denaturing formaldehyde gel and transfer to nylon of 2 µg poly $(A)^+$ RNA obtained from normal human white blood cells, colon, small bowel, ovary, testis, prostate, thymus and spleen and from esophagus, stomach, intestine, colon, uterus, placenta, bladder and adipose tissue. The probe used for all Northern blots was a fragment (SEQ ID NO:5) from the initial PAR clone. This fragment was obtained by PCR amplification using the primers 5'-GCCACCTCTGCTGGTTGCTCTG-3' (SEQ ID NO:3; sense) and 5'-CCAGGATACAAGGGTG-GAATGTA-3' (SEQ ID NO:4; antisense). Fifty nanograms plasmid DNA containing PAR insert were subjected to 35 PCR cycles consisting in denaturation at 95° C. for 1 minute, annealing at 60° C. for 1 minutes and extension at 72° C. for 30 seconds for the first cycle, followed by denaturation at 95° C. for 30 seconds, annealing at 60° C. for 30 seconds and extension at 72° C. for 30 seconds, for 34 cycles with a final extension at 72° C., for 7 minutes. The PCR product was purified with QIAquick purification kit (Qiagen, Chatsworth, Calif.), sequenced with one of the PCR primers and shown to have the expected PAR sequence. This fragment was labeled by the random primer method with $\alpha^{32}P$ dCTP, 6,000 Ci/mmole (NEN Life Science Products, Boston, Mass.) to a specific activity of more than $3\times10^8$ cpm/µg. The hybridization procedure followed the manufacturer's protocol. Following hybridization to the PAR probe, the blots were rehybridized to a 28S ribosomal RNA oligo probe (Clontech, Palo Alto, Calif.).

For other Northern blots, total RNA was extracted from MCF-7 and T47 D breast carcinoma cells and LNCaP, LNCaP-OM, PC3 and DU 145 prostatic cancer cells by Chomszinski's method (Chomszynski and Sacchi, 1987, Anal. Biochem. 162: 156-159). Normal breast and prostatic tissue total RNA were purchased from Clontech (Palo Alto, Calif.) Northern blots were prepared as described in Platica et al. (1989, Proc. Soc. Exptl. Biol. and Med. 192: 95-97) Briefly, thirty micrograms total RNA from normal and malignant cells were subjected to electrophoresis on a 1.2% denaturing formaldehyde gel and transfer to nylon membranes. After prehybridization, the hybridization was carried out in 6×SSC, 50% formamide, 2× Denhardt's solution, 50 µg/ml sonicated salmon sperm DNA and $2\times10^6$ cpm/ml radioactive PAR probe, at 42° C., overnight. The washings were performed in 2×SSC/0.1% SDS for 10 minutes at room temperature and in 0.1×SSC/0.1% SDS at 65° C., for 1 hour. The PAR expression in breast primary tumors was studied with a Northern blot (Invitrogen, Carlsbad, Calif.) containing 20 µg total RNA per lane extracted from four different human breast tumors and their normal tissue counterparts. This blot was hybridized to PAR probe in the conditions described (Platica et al., 1989, Proc. Soc. Exptl. Biol. and Med. 192 95-97). For the normalization of the amount of RNA in each lane, all Northern blots were hybridized to the 28S ribosomal RNA oligo probe (Clontech Lab, Palo Alto, Calif.).

The autoradiograms were read with the flatbed scanner UMAX Astra 1200 and the intensity of the bands compared using NIH Image software version 1.61.

6.1.5 RNA Dot Blots

A total RNA dot blot (BioChain Institute, San Leandro, Calif.) containing 2 µg total RNA from 24 various normal tissues and their malignant counterparts was hybridized to the PAR probe following the manufacturer's instructions. The normalization for the amount of RNA in each dot was performed by hybridization with the 28S rRNA oligo probe (Clontech Lab, Palo Alto, Calif.).

6.1.6 Androgen Effect on Par Expression in Prostate Cancer Cells

LNCaP and DU 145 cells grown in RPMI 1640 medium supplemented with 10% FCS (Gibco BRL,), were transferred to RPMI medium supplemented with 10% charcoal stripped (cs)-FCS (Cocalico Biol. Inc., PA) for 10 days. The cells at concentrations of $1\times10^5$/ml were divided in 3 groups: the control group cultured in RPMI supplemented with 10% cs-FCS, and 2 other groups which received in addition, R1881 (NEN™ Life Science Products Boston, Mass.), in concentration of $1\times10^{-10}$ M and $1\times10^{-9}$ M, respectively. After 3 days of culture, twenty micrograms of total RNA extracted from each cell group were analyzed by Northern blots hybridized to PAR probe as described.

6.2 Results and Discussion

6.2.1 Isolation of Par cDNA

The subtraction method used in this study was a representational difference analysis (Lisitsyn et al., 1993, Science 259: 946-951) modified to isolate expressed genes. One of our modifications consisted in using mRNA from driver cells instead of ds cDNA as in the original method and in the Hubank and Schatz's RDA adaptation (Hubank and Schatz, 1994, Nucleic Acids Research 22: 5640-5648) for subtraction of expressed genes. During the initial PCR annealing step the driver mRNA formed stable hybrids with the complementary DNA sequences from the tester cDNA and prevented their amplification. The cDNA strands homologous to driver mRNA were amplified linearly. The amplification of genes expressed only in tester cells was not affected by driver mRNA and occurred exponentially. The difference between the rate of PCR amplification of these two cDNA populations allowed the detection of the genes overexpressed, or present only in tester cells. The second modification was the use of a long linker (Ba) allowing repeated PCR amplification with nested primers and obviating the need for changing the primers after each amplification step.

The subtraction was performed between the cDNA library prepared from the androgen resistant LNCaP-OM subline and the mRNA extracted from androgen sensitive LNCaP cells. The LNCaP-OM subline was purposely developed in our laboratory from the androgen sensitive LNCaP cells in order to minimize the chance of isolating genes not involved in androgen resistance when subtraction was performed.

From a limited analysis of the subtracted library six clones selected at random were studied. Five of these clones were expressed at least 2 fold higher in LNCaP-OM compared with LNCaP cells indicating that this method isolated predominantly genes overexpressed in tester cells. These clones were sequenced and one of them, PAR, which was found to be a novel gene is disclosed herein.

Compared to the original RDA method (Lisytsin, et al., 1993, Science 259: 946-951) and Hubank and Schatz's adaptation for the subtraction of the expressed genes (Hubank and Schatz, 1994, Nucleic Acids Research 22: 5640-5648) our method is much simpler, it does not require the preparation of the second cDNA library from the driver cells and repeated ligation of new primers for each round of PCR amplification. Although it is more labor intensive than the differential display (Liang and Pardee, 1992, Science 257: 967-971), our method is able to isolate simultaneously a large number of genes differentially expressed in tester cells. In addition, the insert analysis and preparation of probes from the subtracted clones in our method, can be easily obtained by direct sequencing and PCR amplification of the phage clones with λ gt11 primers.

6.2.2 Isolation of the Full Length Par cDNA Clone

The initial PAR cDNA clone obtained from the subtracted library included the poly A tail and 690 bp from 3' region of the gene. The entire insert was PCR amplified with λ gt11 forward and reverse primers and used to screen the cDNA library from LNCaP-OM. From eight positive clones, the clone with the largest insert was sequenced and found to have 954 bp including PAR initial sequence. In order to map the transcription start site of PAR mRNA the 5' RACE assay was performed. The sequence obtained by RACE included 174 nucleotides from PAR cDNA 5' extremity and a new sequence of 26 nucleotides, upstream of the 5' end, which was added to the final PAR cDNA sequence.

6.2.3 Analysis of Par cDNA Sequence

The PAR cDNA clone was analyzed with MacDNASIS Pro Sequence Analysis Software (Hitachi Software, San Bruno, Calif.) version 3.6 and BLAST program (NIH).

The complete PAR cDNA sequence (SEQ ID NO:1; FIG. 2) contains 1037 nucleotides including a poly A tail and a polyadenylation signal located about 20 nucleotides upstream of poly A tail starting site.

The search in GenBank database with BLAST program revealed that PAR 3' cDNA region beginning at nucleotide 555 has 99% homology with several EST clones with accession number R01857, AI354691, and AI333776.

6.2.4 Par Expression in Normal Tissues

Figure 3:
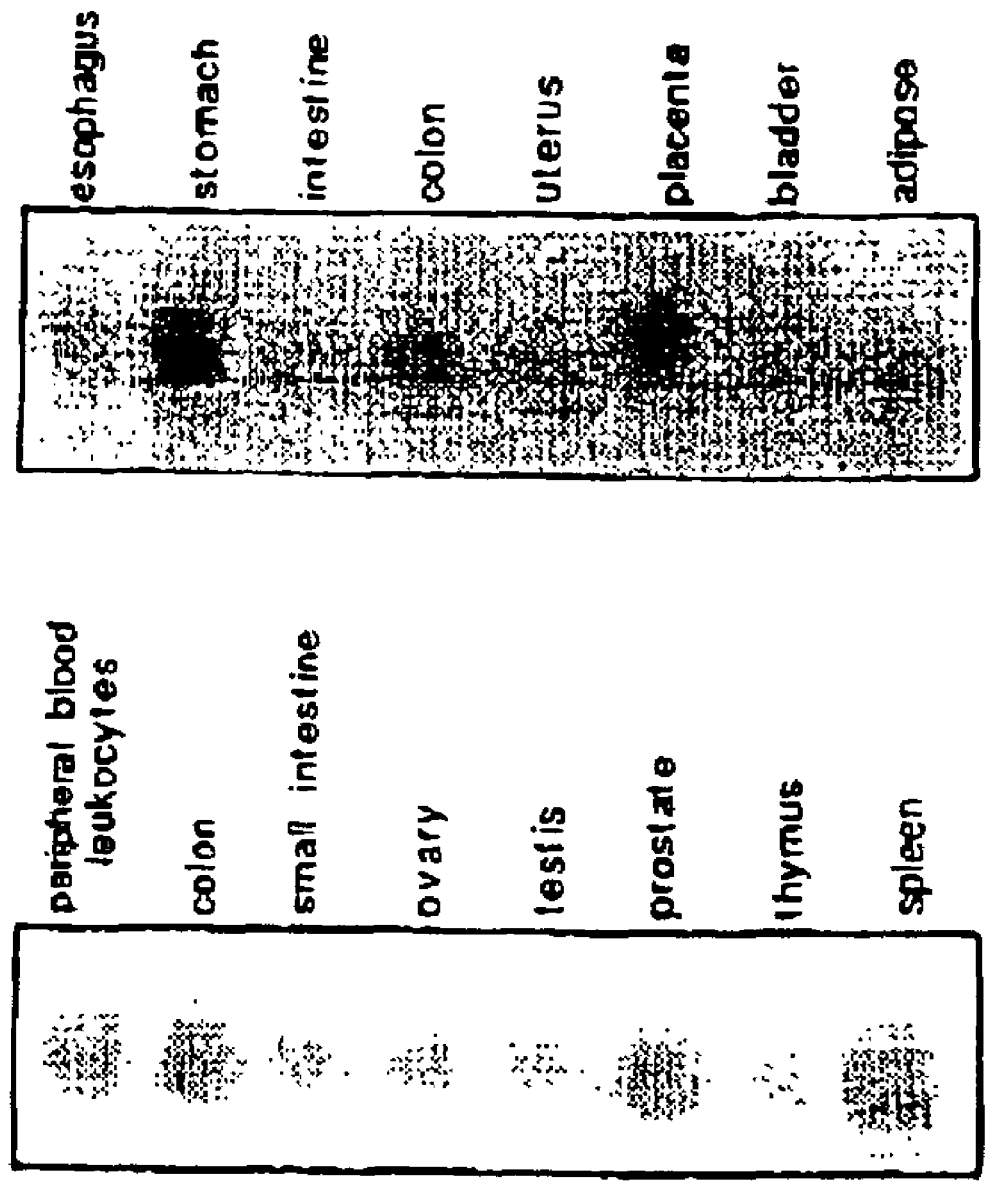

PAR was detected on Northern blots as a single 1.0 kb mRNA species in all 15 normal tissues examined, with higher levels of expression in prostate, colon, spleen, stomach and placenta and lower levels in thymus, esophagus, small bowel, testis, ovary and adipose tissues (FIG. 3). There were 2-3 fold variations among PAR mRNA levels in tissues studied. Normalization with 28S probe showed an equal distribution of poly(A)$^+$ RNA in all lanes.

In addition, on the dot blot (FIG. 4) PAR was expressed in all 24 normal tissues with the lowest levels in brain and Non Hodgkin's lymphoma,

6.2.5 Par Expression in Malignant Tissues

Figure 5:
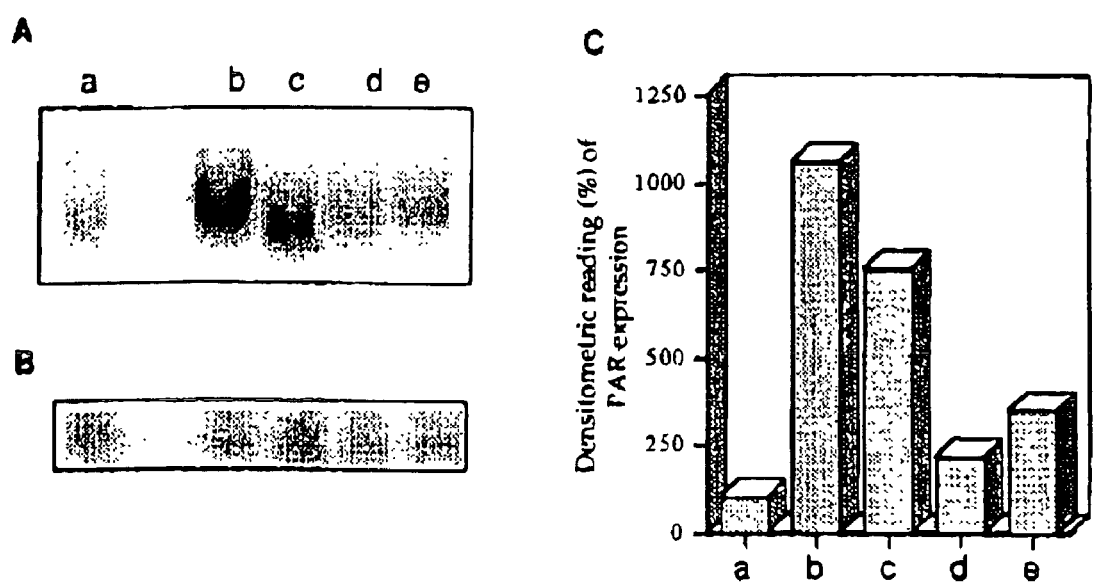

PAR gene mRNA was overexpressed in all human prostate cancer cell lines studied (LNCaP, DU145, PC3 and LNCaP-OM), compared to the normal prostate tissue. Its level of expression was the lowest LNCaP (2 fold), followed by PC3 (3 fold), LNCaP-OM (6 fold), and DU 145 (11 fold) (FIG. 5). In addition, PAR expression was higher in androgen resistant prostatic cancer cell lines DU145, PC3 and LNCaP-OM, compared to androgen sensitive prostate cancer cell line LNCaP, by 4.6, 1.5 and 3.2 fold, respectively, as shown by Northern blot analysis.

Figure 6:
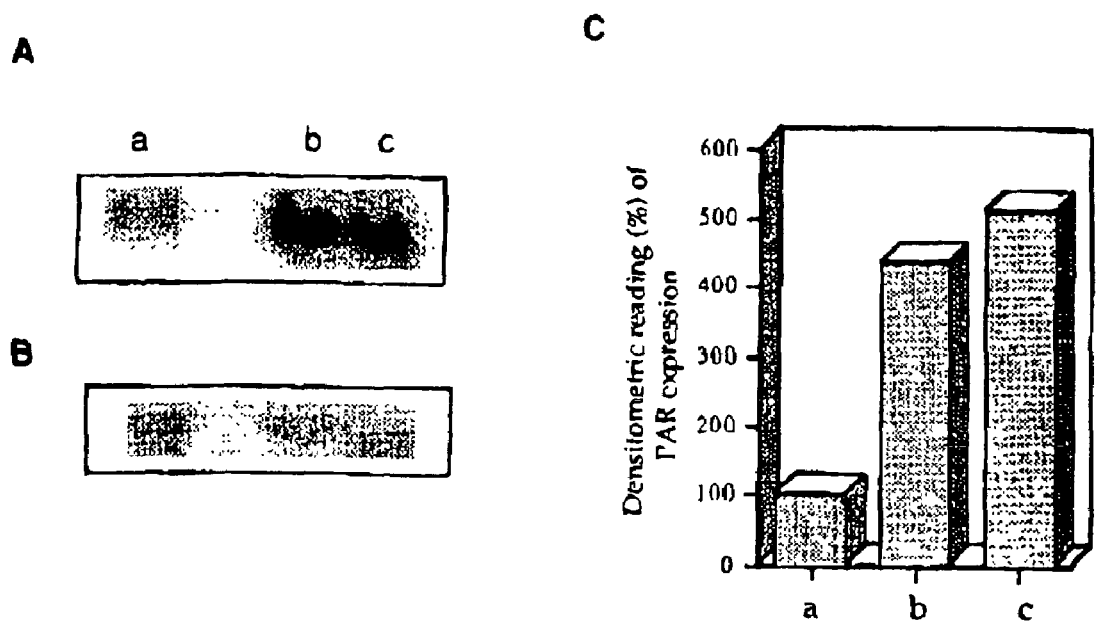

Similarly, the expression of this gene was found 4.5 and 5.2 fold higher in breast cancer cell lines MCF-7 and T47 D, respectively, compared to normal breast RNA (FIG. 6).

Figure 7:
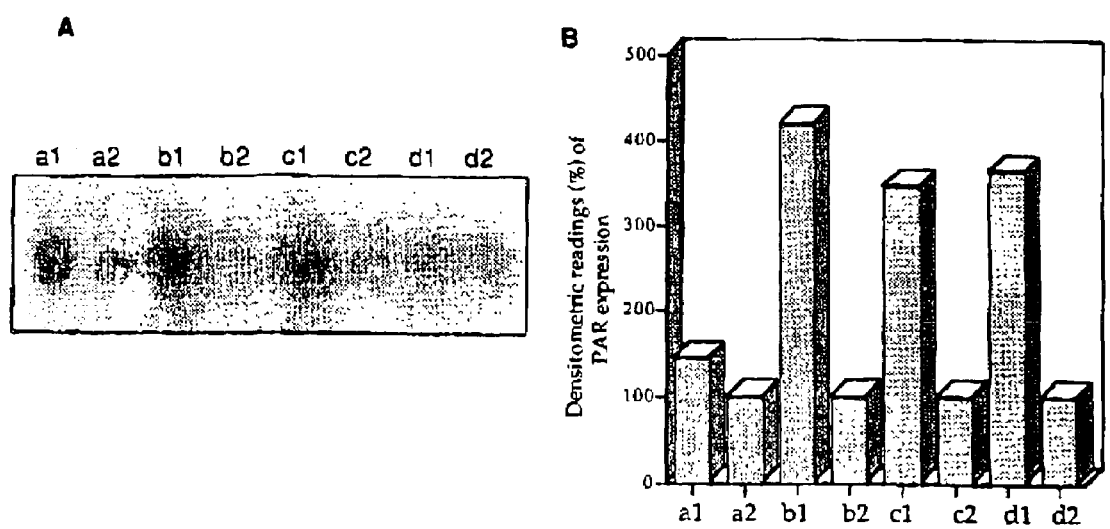

In 4 primary breast tumors the PAR expression was between 1.5 and 4.2 fold higher in comparison with the normal breast tissue obtained from the same patient (FIG. 7).

A dot blot containing RNA from 24 malignant tissues and their normal counterparts showed that in 16 malignant tissues (67%) PAR was overexpressed, in 6 (25%) its expression was almost equal in normal and malignant specimens, and only in 2 (2%) malignant tissues the PAR expression was lower than in normals (FIG. 4). Normalization with 28S probe showed an equal distribution of RNA in all dots.

6.2.6 The Par Gene is Amplified in Malignant Cells

In additional experiments, Southern blots were prepared using DNA from the T47 D breast cancer cell line, the DU 145 prostate cancer cell line, normal breast and prostate tissues, digested with EcoR1. The Southern blots were then hybridized with radiolabeled PAR probe (SEQ ID NO:5) and autoradiographically exposed. Bands corresponding to the PAR gene were quantified by densitometry. Then the filters were washed to remove the PAR probe and rehybridized with probe corresponding to the constitutive TCII (transcarbamine II) gene, exposed autoradiographically, and bands corresponding to the TCII gene were quantified by densitometry. For each hybridization, the conditions were according to the Clontech instructions for ExpressHyb™ hybridization solutions (Clontech Laboratories, Palo Alto, Calif.), specifically, prehybridization for 30 minutes at 60° C., followed by hybridization for 1 hour at 60° C., and then washing first at room temperature for 30 minutes in 2×SSC, 0.05% SDS, and then at 50° C. for 40 minutes in 0.1×SSC, 0.1% SDS. When the densitometry readings for the PAR gene (using the TCII gene as an internal control) in the normal and malignant tissues were compared, whereas the ratio of PAR signal to TCII signal in normal breast and prostate tissues was approximately 1:1, the PAR/TCII ratio in T47 D breast cancer cells and DU 145 prostate cancer cells was >2:1, indicating that the PAR gene may be amplified in these malignant cells.

6.2.7 Regulation of Par Expression by Androgens

Figure 8:
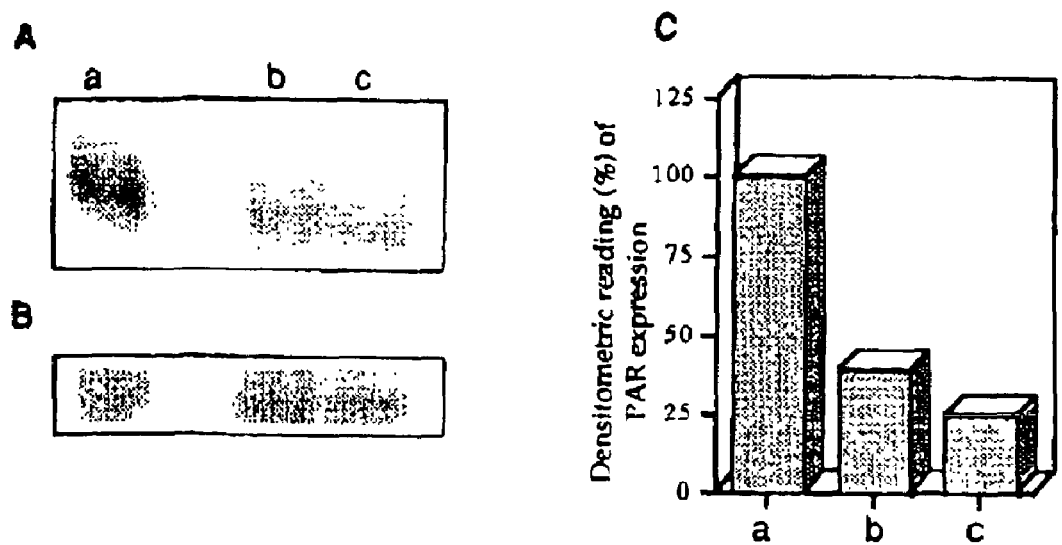

The effect of androgens on PAR expression in prostate cancer cells was also studied. Treatment of LNCaP cells with R1881 in concentration of $1 \times 10^{-10}$ M and $1 \times 10^{-9}$ M for 3 days, decreased PAR expression by 3 and 4 fold respectively, as determined by Northern blot analysis (FIG. 8). The treatment with R1881 had no effect on PAR expression in androgen resistant cells DU 145.

Similar results were obtained using RT-PCR instead of Northern blots (Platica et al., Mar. 15-18, 1998, International Symposium on Biology of Prostate Growth, NIH, Bethesda, Md.). The androgens, tested in a wide range of concentrations ($1 \times 10^{8}$-$1 \times 10^{-11}$M), for different time intervals, had no effect on PAR expression in any androgen resistant cell lines studied (DU 145, PC3 and LNCaP-OM), compared to control, untreated cells. In contrast, under the same experimental conditions, the androgens inhibited the PAR expression in the hormone sensitive LNCaP prostate cancer cells.

6.2.8 Par Has a Proliferative Effect on Cancer Cells

An anti-sense-strand PAR gene, as contained in the plasmid, was stably transfected into NIH 3T3 cells, T47 D breast cancer cells, and DU 145 prostate cancer cells. In all cases, the proliferation rate of the cells, as measured by tritiated thymidine uptake and MTT assay, decreased in the transfected cells (relative to untransfected control). In contrast, when a sense-strand PAR gene, as contained in the plasmid pCMV-Script™, was transfected into NIH-3T3 cells, proliferation of the cells increased. These results are consistent with a role of the PAR gene and its product in the cell cycle and malignant transformation.

Various publications are cited herein, the contents of which are hereby incorporated by reference in their entireties.

What is claimed is:

1. A method of inhibiting the proliferation of a cell, comprising inhibiting prostate androgen regulated (PAR) protein in said cell, wherein said inhibiting comprises contacting said PAR protein of said cell with an antibody preparation, wherein said antibody preparation comprises an antibody immunologically reactive with a PAR protein comprising of SEQ ID NO:2; and wherein said antibody preparation binds to and inhibits said PAR protein.

2. The method of claim 1, wherein said cell is a malignant cell.

3. The method of claim 1, wherein said cell is a cancer cell selected from the group consisting of a prostate cell, a breast cell, a brain cell, gallbladder cell, an ovarian cell, a lung cell, a stomach cell, a kidney cell, a uterus cell, a duodenum cell, a ureter cell, a thyroid cell, a colon cell, a bladder cell, an adrenal cell, a rectum cell, a thymus cell, a liver cell, and a lymphoma cell.

4. The method of claim 1, wherein said cell is a non-malignant proliferative cell.

5. The method of claim 4, wherein said cell is a vascular endothelial cell.

6. The method of claim 1, wherein said antibody preparation comprises a polyclonal antibody preparation.

7. The method of claim 1, wherein said antibody preparation consists essentially of a monoclonal antibody preparation.

8. The method of claim 1, wherein said antibody preparation comprises a single chain antibody preparation.

9. The method of claim 1, wherein said antibody comprises a chimeric antibody.

10. The method of claim 3, wherein said cell is a breast cancer cell.

11. The method of claim 3, wherein said cell is a prostate cancer cell.

12. A method of inhibiting the malignant transformation of a cell comprising inhibiting PAR protein of said cell, wherein said inhibiting comprises contacting said PAR protein of said cell with an antibody preparation, wherein said antibody preparation comprises an antibody immunologically reactive with a PAR protein comprising of SEQ ID NO:2; and wherein said antibody preparation binds to and inhibits said PAR protein.

13. The method of claim 12, wherein said cell is a breast cancer cell.

14. The method of claim 12, wherein said breast cancer cell is a primary breast cancer cell.

15. The method of claim 12, wherein said cell is a prostate cancer cell.

16. A method of treating breast cancer in a subject, comprising identifying the subject having an increased expression of PAR protein in the breast cancer cells:
   a) contacting cells of said subject with an anti-PAR antibody preparation,
   polypeptide
   variant
   wherein said antibody preparation comprises an antibody immunologically reactive with a PAR protein comprising of SEQ ID NO:2; and wherein said antibody preparation binds to and inhibits said PAR protein.

17. The method of claim 16, wherein said antibody preparation comprises a polyclonal antibody preparation.

18. The method of claim 16, wherein said antibody preparation comprises a monoclonal antibody preparation.

19. A method of treating prostate cancer in a subject, comprising:
   diagnosing
   a) contacting the cells of said subject with an anti-PAR antibody preparation,
   wherein said antibody preparation comprises an antibody immunologically reactive with a PAR protein comprising of SEQ ID NO:2; and wherein said antibody preparation binds to and inhibits said PAR protein.

20. The method of claim 19, wherein said antibody preparation comprises a polyclonal antibody preparation.

21. The method of claim 19, wherein said antibody preparation comprises a monoclonal antibody preparation.

22. The method according to claim 1 wherein said antibody preparation inactivates said PAR protein.

23. The method according to claim 12 wherein said antibody preparation inactivates said PAR protein.

24. The method according to claim 16 wherein said antibody preparation inactivates said PAR protein.

25. The method according to claim 19 wherein said antibody preparation inactivates said PAR protein.

* * * * *

UNITED STATES PATENT AND TRADEMARK OFFICE
CERTIFICATE OF CORRECTION

| | |
|---|---|
| PATENT NO. | : 7,510,707 B2 |
| APPLICATION NO. | : 10/178389 |
| DATED | : March 31, 2009 |
| INVENTOR(S) | : Micsunica Platica et al. |

It is certified that error appears in the above-identified patent and that said Letters Patent is hereby corrected as shown below:

In the Claims:

At Column 23, lines 6-7, "polypeptide variant" should be deleted

Signed and Sealed this
Nineteenth Day of July, 2011

David J. Kappos
*Director of the United States Patent and Trademark Office*

SEQUENCE LISTING

<160> NUMBER OF SEQ ID NOS: 10

<210> SEQ ID NO 1
<211> LENGTH: 1037
<212> TYPE: DNA
<213> ORGANISM: Homo sapiens

<400> SEQUENCE: 1

| | | |
|---|---|---|
| cgacgcggaa gactataagc cccagcgggc gacgaccgaa cgcccccggg aacaccgggc | 60 |
| cccgagctcg gtcccgcgcc cgaggatcct ccacggggct agatggctgc gtcgggggcg | 120 |
| ggagcggagg tgagcgggcg ctagggccgc gagccccgc cggcccttcc tccagcgccc | 180 |
| tgcggacccc gcagaaggcg ctcgcctccc tagcccgcaa caacatatcg attttctcg | 240 |
| ctgtggcaac ggggacgtcc tgatagatcc tctgctccaa taggcaactc cggccttccc | 300 |
| tgccctgacc tggaacctct ggagggctg cagagtaagt gccgcctctg cgctccgacg | 360 |
| gaggcacgag gcctgtggag taggtccctc tgttccgaca ggtgcgacac ttggcgctcc | 420 |
| atgcttgcgg gtgccgggag gcctggcctc ccccagggcc gccacctctg ctggttgctc | 480 |
| tgtgctttca ccttaaagct ctgccaagca gaggctcccg tgcaggaaga gaagctgtca | 540 |
| gcaagcacct caaatttgcc atgctggctg gtggaagagt ttgtggtagc agaagagtgc | 600 |
| tctccatgct ctaatttccg ggctaaaact accctgagt gtggtccac aggatatgta | 660 |
| gagaaaatca catgcagctc atctaagaga aatgagttca aaagctgccg ctcagctttg | 720 |
| atggaacaac gcttattttg gaagttcgaa ggggctgtcg tgtgtgtggc cctgatcttc | 780 |
| gcttgtcttg tcatcattcg tcagcgacaa ttggacagaa aggctctgga aaaggtccgg | 840 |
| aagcaaatcg agtccatata gctacattcc acccttgtat cctgggtctt agagacccta | 900 |
| tctcagacag tgaaagtgaa atggactgat ttgcactctt ggttctttgg agccttgtgg | 960 |
| tggaatcccc ttttccccat cttcttcttt cagatcatta atgagcagaa taaaagagt | 1020 |
| aaaatggtaa aaaaaaa | 1037 |

<210> SEQ ID NO 2
<211> LENGTH: 146
<212> TYPE: PRT
<213> ORGANISM: Homo sapiens

<400> SEQUENCE: 2

Met Leu Ala Gly Ala Gly Arg Pro Gly Leu Pro Gln Gly Arg His Leu
 1               5                  10                  15
Cys Trp Leu Leu Cys Ala Phe Thr Leu Lys Leu Cys Gln Ala Glu Ala
            20                  25                  30
Pro Val Gln Glu Glu Lys Leu Ser Ala Ser Thr Ser Asn Leu Pro Cys
        35                  40                  45
Trp Leu Val Glu Glu Phe Val Val Ala Glu Cys Ser Pro Cys Ser
    50                  55                  60
Asn Phe Arg Ala Lys Thr Thr Pro Glu Cys Gly Pro Thr Gly Tyr Val
65                  70                  75                  80
Glu Lys Ile Thr Cys Ser Ser Ser Lys Arg Asn Glu Phe Lys Ser Cys
                85                  90                  95
Arg Ser Ala Leu Met Glu Gln Arg Leu Phe Trp Lys Phe Glu Gly Ala
            100                 105                 110
Val Val Cys Val Ala Leu Ile Phe Ala Cys Leu Val Ile Ile Arg Gln
        115                 120                 125

```
Arg Gln Leu Asp Arg Lys Ala Leu Glu Lys Val Arg Lys Gln Ile Glu
    130                 135                 140

Ser Ile
145

<210> SEQ ID NO 3
<211> LENGTH: 22
<212> TYPE: DNA
<213> ORGANISM: Homo sapiens

<400> SEQUENCE: 3
gccacctctg ctggttgctc tg                                             22

<210> SEQ ID NO 4
<211> LENGTH: 23
<212> TYPE: DNA
<213> ORGANISM: Homo sapiens

<400> SEQUENCE: 4
ccaggataca agggtggaat gta                                            23

<210> SEQ ID NO 5
<211> LENGTH: 427
<212> TYPE: DNA
<213> ORGANISM: Homo sapiens

<400> SEQUENCE: 5
gccacctctg ctggttgctc tgtgctttca ccttaaagct ctgccaagca gaggctcccg    60
tgcaggaaga gaagctgtca gcaagcacct caaatttgcc atgctggctg gtggaagagt   120
ttgtggtagc agaagagtgc tctccatgct ctaatttccg ggctaaaact accctgagt    180 gtggtcccac aggatatgta gagaaaatca catgcagctc atctaagaga aatgagttca   240
aaagctgccg ctcagctttg atggaacaac gcttattttg gaagttcgaa ggggctgtcg   300
tgtgtgtggc cctgatcttc gcttgtcttg tcatcattcg tcagcgacaa ttggacagaa   360
aggctctgga aaaggtccgg aagcaaatcg agtccatata gctacattcc accttgtat    420 cctgggt                                                             427

<210> SEQ ID NO 6
<211> LENGTH: 36
<212> TYPE: DNA
<213> ORGANISM: Homo sapiens
<220> FEATURE:
<221> NAME/KEY: misc_structure
<222> LOCATION: (0)...(0)
<223> OTHER INFORMATION: LINKER, 3'-5'

<400> SEQUENCE: 6
cggtcgacct atcgattctg gaaccttcag aggtct                              36

<210> SEQ ID NO 7
<211> LENGTH: 33
<212> TYPE: DNA
<213> ORGANISM: Homo sapiens

<400> SEQUENCE: 7
cctctgaagg ttccagaatc gataggtcga ccg                                 33

<210> SEQ ID NO 8
<211> LENGTH: 20
<212> TYPE: DNA
```

-continued

```
<213> ORGANISM: Homo sapiens

<400> SEQUENCE: 8
gttccagaat cgataggtcg                                           20

<210> SEQ ID NO 9
<211> LENGTH: 438
<212> TYPE: DNA
<213> ORGANISM: Homo sapiens

<400> SEQUENCE: 9
atgcttgcgg gtgccgggag gcctggcctc ccccagggcc gccacctctg ctggttgctc    60
tgtgctttca ccttaaagct ctgccaagca gaggctcccg tgcaggaaga gaagctgtca   120
gcaagcacct caaatttgcc atgctggctg gtggaagagt ttgtggtagc agaagagtgc   180
tctccatgct ctaatttccg ggctaaaact acccctgagt gtggtcccac aggatatgta   240
gagaaaatca catgcagctc atctaagaga aatgagttca aaagctgccg ctcagctttg   300
atggaacaac gcttattttg gaagttcgaa ggggctgtcg tgtgtgtggc cctgatcttc   360
gcttgtcttg tcatcattcg tcagcgacaa ttggacagaa aggctctgga aaaggtccgg   420
aagcaaatcg agtccata                                              438

<210> SEQ ID NO 10
<211> LENGTH: 33
<212> TYPE: DNA
<213> ORGANISM: Homo sapiens
<220> FEATURE:
<221> NAME/KEY: misc_structure
<222> LOCATION: (0)...(0)
<223> OTHER INFORMATION: LINKER, 5'-3'

<400> SEQUENCE: 10
cctctgaagg ttccagaatc gataggtcga ccg                             33
```